United States Patent [19]

Elliott et al.

[11] Patent Number: 4,884,567

[45] Date of Patent: Dec. 5, 1989

[54] METHOD FOR TRANSVENOUS IMPLANTATION OF OBJECTS INTO THE PERICARDIAL SPACE OF PATIENTS

[75] Inventors: Clyde D. Elliott, Mountain Brook, Ala.; Donald M. Cohen, Encino, Calif.

[73] Assignees: Dimed Inc., Birmingham, Ala.; Siemens- Pacesetter, Inc., Sylmar, Calif.

[21] Appl. No.: 128,326

[22] Filed: Dec. 3, 1987

[51] Int. Cl.$^4$ ............................................. A61B 17/00
[52] U.S. Cl. ........................... 128/303 R; 128/419 D; 128/334 R; 128/785
[58] Field of Search ............... 128/419 P, 419 D, 785, 128/786, 303 R, 334 R, 334 L; 604/51, 52

[56] References Cited

U.S. PATENT DOCUMENTS 4,471,777  9/1984  McCorkle, Jr. ................. 128/303 R

FOREIGN PATENT DOCUMENTS 2032278  5/1980  United Kingdom ............... 128/785

OTHER PUBLICATIONS

Mills et al., *Current Emergency Diagnosis and Treatment*, Lange, Medical Publications, pp. 249–250.

*Primary Examiner*—Kyle L. Howell
*Assistant Examiner*—John D. Zele
*Attorney, Agent, or Firm*—John P. White; Peter A. Luccarelli, Jr.

[57] ABSTRACT

The improved transvenous implantation method of the present invention involves entering a vein of a patient, translating through the vein to the patient's cardium atrium, anchoring onto the atrial lateral wall, puncturing the atrial lateral wall and forming a hole therein, exiting the atrium through the hole to the pericardial space and inserting the object into the pericardial space. The present invention also includes a method for the transvenous repair of a wound in the atrial lateral wall.

14 Claims, 9 Drawing Sheets

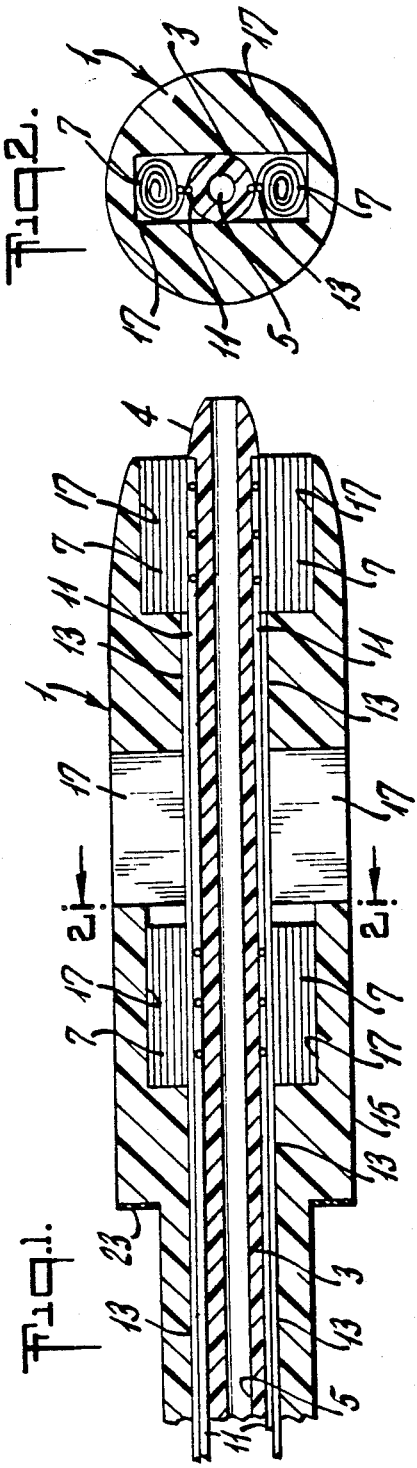

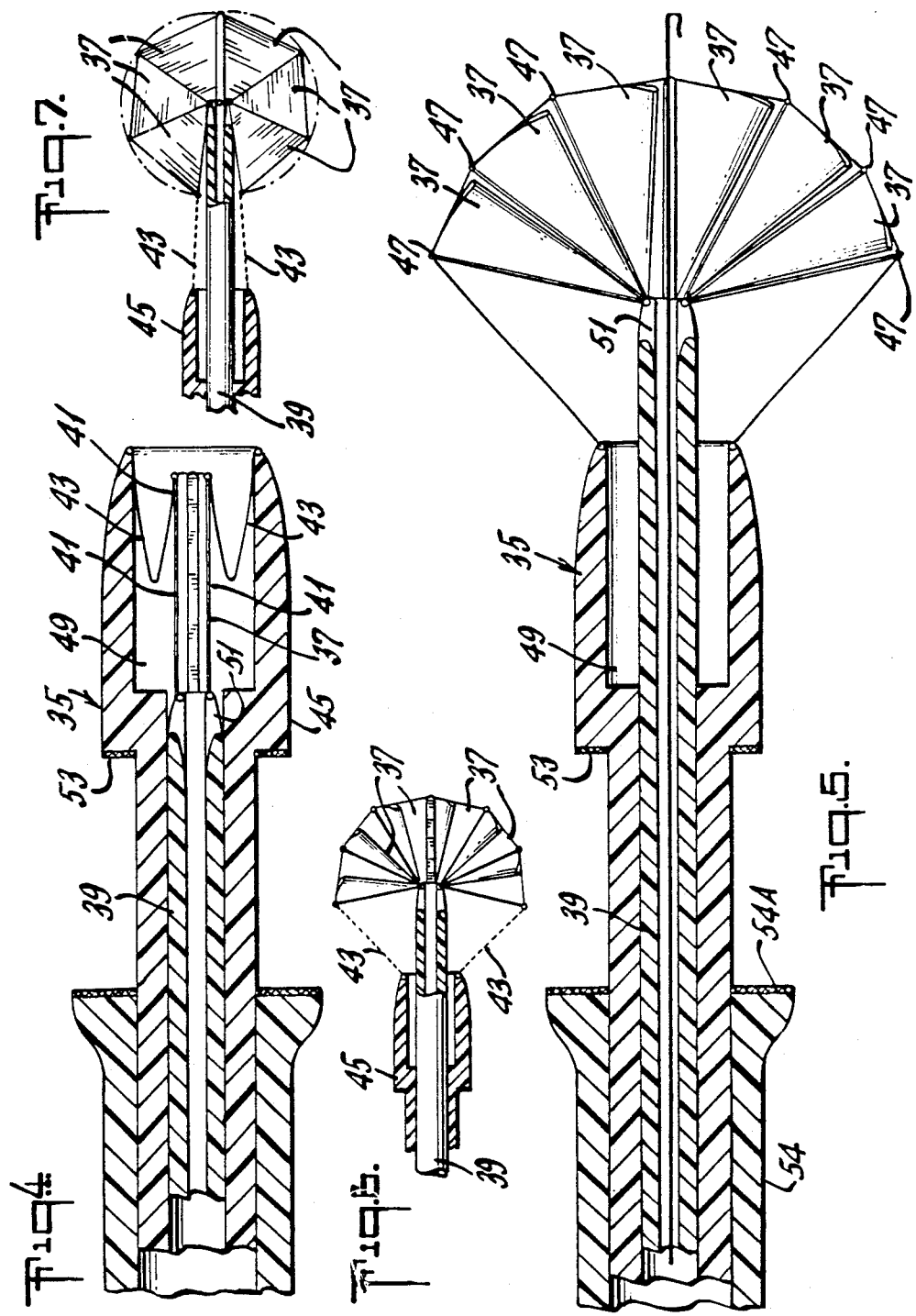

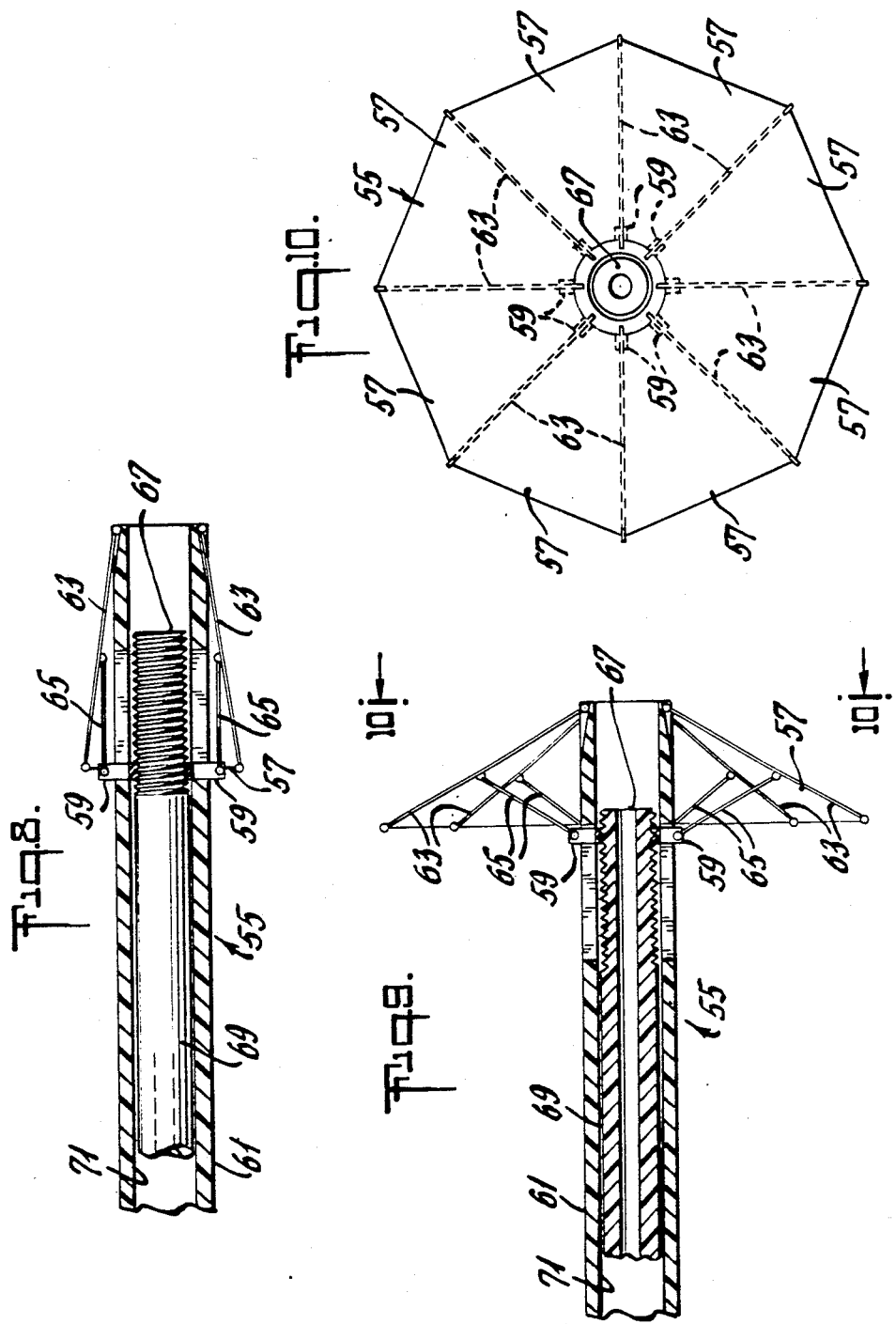

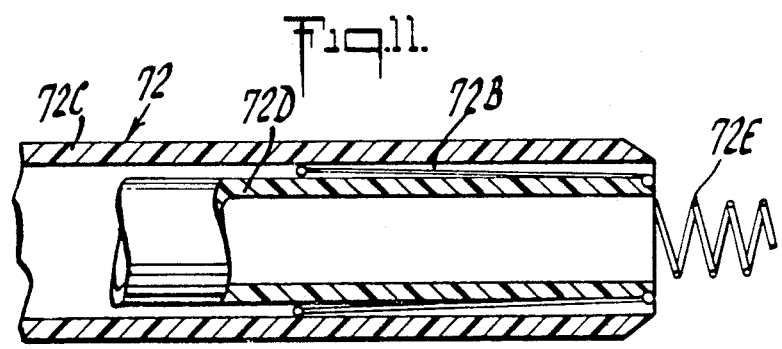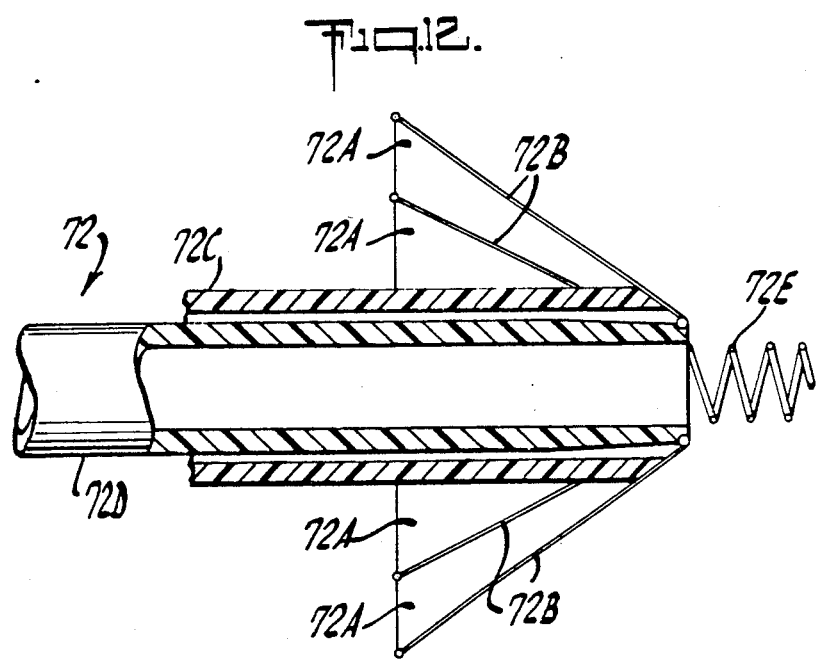

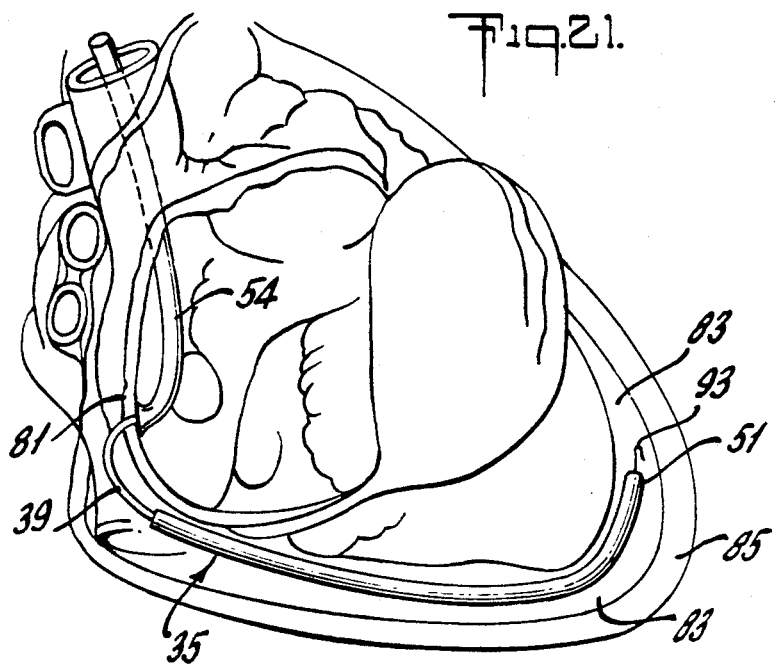
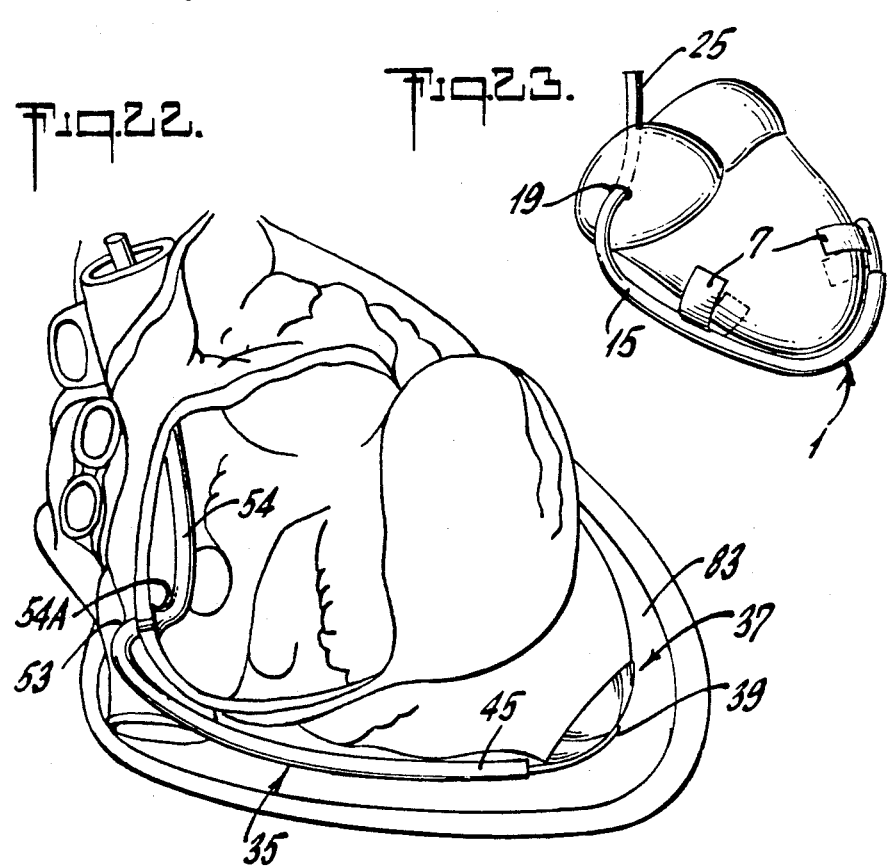

METHOD FOR TRANSVENOUS IMPLANTATION OF OBJECTS INTO THE PERICARDIAL SPACE OF PATIENTS

BACKGROUND OF THE INVENTION

This invention relates generally to defibrillator systems with implantable cardiac leads and particularly implantable cardiac defibrillator leads and methods for the transvenous implantation of objects into the pericardial space of patients.

There are large numbers of patients suffering from severe ischemic heart disease having arterial blockage that places them at risk for life-threatening ventricular arrhythmias. To minimize the chance of death for those patients, there has been a long-felt need in the medical community for a portable but reliable defibrillator unit that could accompany the patients. There has been another long-felt need in the medical community for a defibrillator system that could detect the onset of any arrythmia and automatically defibrillate the patient.

Unfortunately, while defibrillator hardware technology has advanced significantly, there have been serious shortcomings in defibrillator lead electrode design that have inhibited development of automatic portable defibrillators. First, ideal positioning of defibrillator leads now requires a thoroctomy and many candidates for an automatic defibrillator are not good candidates for massive chest surgery.

Known transvenously implantable endocardial leads used in pacer systems have adequate electrode surface area for transferring the large quantities of electrical energy used during defibrillation, but they can undesirably cause severe thermal burns to the patient as well as cause high defibrillation thresholds or large volume gas bubbles in the patient's cardiovascular system, if they are used for defibrillation.

External defibrillator leads are not energy efficient because large amounts of energy are dissipated by body tissue between the skin surface and the endocardium. Electrodes optimally inserted in the pericardial space over the right and left ventricles would presumably minimize power consumption and allow development an implantable defibrillator system carried by the patient in the same manner as a cardiac pacer.

It is an object of the present invention to devise a method for transvenous implantation of an object, such as a defibrillator system cardiac lead, into the pericardial space of a patient.

SUMMARY OF THE INVENTION

These objects have been attained with the cardiac defibrillator system with implantable cardiac leads and method of transvenous implantation as described and claimed in the present invention. The cardiac leads described and claimed herein are especially suitable for use as ventricular defibrillator leads and some of them may be implanted transvenously into the pericardial space of a patient using the implantation methods of the present invention. Other cardiac leads described and claimed herein may be implanted transvenously into an atrium of a patient.

The present invention relates to a method for the transvenous implantation of a device in a patient through a vein having a lumen into a pericardial space surrounding a cardium having an atrium and an atrial lateral wall comprising entering the vein; translating through the vein lumen to the atrium; anchoring onto the atrial lateral wall; puncturing the atrial lateral wall and forming a hole therein; exiting the atrium through the hole to the pericardial space; and inserting the device into the pericardial space.

The present invention also relates to a method for the transvenous repair of a wound in the atrial lateral wall of a patient through a vein having a lumen comprising entering the vein; translating through the vein lumen to an atrium of the patient's cardium with a catheter; anchoring the catheter onto the atrial lateral wall over the wound; translating a blood clot through the catheter to the wound; compressing the blood clot into the wound; and removing the catheter.

BRIEF DESCRIPTION OF THE FIGURES

FIG. 1 is a partial cross-sectional, plan view of one embodiment of a cardiac lead of the present invention, showing the electrodes in a collapsed position.

FIG. 2 is a sectional view of the cardiac lead shown in FIG. 1, taken along section 2—2 thereof.

FIG. 3 is a partial cross-sectional, plan view of the cardiac lead shown in FIG. 1, showing the electrodes in an extended position.

FIG. 4 is a partial cross-sectional plan view of another embodiment of a cardiac lead of the present invention, showing the electrode in a collapsed position.

FIG. 5 is a partial cross-sectional, plan view of the cardiac lead shown in FIG. 4, showing the electrode in a partially extended position.

FIG. 6 is a partial cross-sectional, plan view of the cardiac lead shown in FIGS. 4 and 5, showing the electrode in a further partially extended position.

FIG. 7 is a partial cross-sectional, plan view of the cardiac lead shown in FIGS. 4-6, showing the electrode in the fully extended position.

FIG. 8 is a partial cross-sectional, plan view of another embodiment of a cardiac lead of the present invention, showing the electrode in a collapsed position.

FIG. 9 is a partial cross-sectional, plan view of the cardiac lead shown in FIG. 8, showing the electrode in an extended position.

FIG. 10 is an end view of the cardiac lead shown in FIG. 9.

FIG. 11 is a partial cross-sectional, plan view of another embodiment of a cardiac lead of the present invention, showing the electrode in a collapsed position.

FIG. 12 is a partial cross-sectional, plan view of the cardiac lead shown in FIG. 11, showing the electrode in an extended position.

FIG. 19 is a schematic view of the right atrium and pericardial sac, showing a guide wire in the pericardial space.

FIG. 21 is a schematic view similar to FIG. 19, showing the remainder of the cardiac lead of the present invention inserted into the pericardium, after removal of the sheath catheter.

FIG. 22 is a schematic view similar to FIG. 14, showing the expansion of an electrode into the pericardial space.

FIG. 23 is a schematic elevational cut-away view of a cardium without the pericardial sac, showing placement of left and right ventricular electrodes of a cardiac lead of the present invention directly on the endocardium.

DETAILED DESCRIPTION OF THE INVENTION

Figure 13:
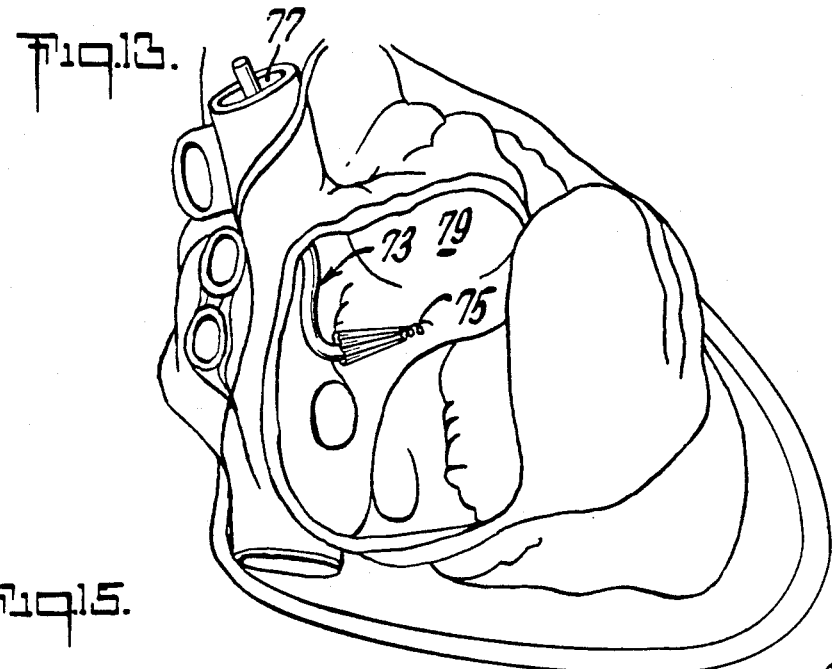
FIG. 13 is a schematic elevational cut-away view of a right atrium, showing another embodiment of a cardiac lead of the present invention, during implantation.

The present invention includes a defibrillator system comprising at least one cardiac lead for implantation into a cardiovascular system of a patient having an elongated first member having a tip on one end thereof, an implantable electrode coupled to the first member and expandable from a collapsed position generally in contact with the lead to an extended position generally away from the lead, and means for expanding the implantable electrode from the collapsed position to the extended position, the expanding means being coupled to the implantable electrode; and means for transferring electrical energy to the electrode coupled to the cardiac lead.

The defibrillator system means for transferring electrical energy may be implantable in a patient's body and may have a battery for storing electrical energy. The defibrillator system may also have a cardiac pacer coupled to the means for transferring electrical energy.

It is also desirable for the defibrillator system to comprise means for sensing a cardiac arrythmia of a patient coupled to the means for transferring electrical energy.

The present invention includes a cardiac lead comprising an elongated first member having a tip on one end thereof; an implantable object coupled to the first member and expandable from a collapsed position generally in contact with the lead to an extended position generally away from the lead; and means for expanding the implantable object from the collapsed position to the extended position, the expanding means being coupled to the implantable object.

In some embodiments of the present invention, the cardiac lead also has a middle member nested over the first member proximal the tip and an outer member nested over the first member proximal the middle member. The first member may have an axial bore therethrough.

In the preferred embodiment, the implantable object is a conductive electrode sheet. The electrode sheet may have generally rectangular, generally sector-shaped arc of a circle, or generally circular shaped construction.

The means for expanding is preferably closed ducts on the electrode sheet for receipt of pressurized fluid, but the means for expanding may include at least one rib pivotally coupled to the first member and rib extension means; the rib extension means may include biasing means coupling each rib to the first member, or a wire coupled to the rib and the middle member, so that reciprocating the middle member biases the wire, pivots the ribs and expands the sheet. The rib extension means may include a reciprocable collar nested on the first member proximal to the tip, a stay coupled to the collar and to the rib and means for reciprocably biasing the collar proximal the tip, so that reciprocation of the collar reciprocates the stay and pivots the rib in umbrella-like fashion, thereby extending the electrode sheet. Collar biasing means can include a threaded member coupled to the collar and means for rotation of the threaded member, so that rotation of the threaded member reciprocates the collar proximal the tip. The rib extension means can also include a reciprocable middle member nested over the first member.

In the preferred embodiment, the middle member is reciprocable from a first position proximal the tip to a second position distal the tip and the middle member has at least one cavity therein adapted for receipt of an implantable object, such as an electrode sheet expandable from a collapsed position generally within the middle member cavity when the middle member is proximal the tip to an extended position generally outside the lead when the middle member is reciprocated distal the tip and the implantable object has means for expanding the electrode sheet from the collapsed position to the extended position coupled to the sheet.

The cardiac lead outer member has an end proximal the middle member, with an outer member atrial seal. The outer member atrial seal may have a skirt radially projecting therefrom with a face proximal the middle member having a fabric surface thereon. The middle member has an end proximal the outer member having a middle member atrial seal. The middle member atrial seal may have a skirt radially projecting therefrom, with a face proximal the outer member having a fabric surface thereon.

The cardiac lead may comprise an elongated first member having a tip on one end thereof, and an axial bore therethrough; a conductive electrode sheet coupled to the first member and expandable from a collapsed position generally within the lead to an extended position generally outside the lead; a middle member nested over the first member proximal the tip having at least one cavity therein adapted for receipt of the electrode therein, the middle member being reciprocable from a first position proximal the tip to a second position distal the tip; means for expanding the electrode sheet from the collapsed position to the extended position, the means for expanding being coupled to the sheet; an outer member nested over the first member having an end proximal the middle member; and an outer member atrial seal on the outer member end having a skirt radially projecting therefrom.

The present invention also relates to a method for the transvenous implantation of a device through a vein having a lumen into a pericardial space surrounding a cardium having an atrium and an atrial lateral wall comprising entering the vein; translating through the vein lumen to the atrium; puncturing the atrial lateral wall and forming a hole therein; exiting the atrium through the hole into the pericardial space; and inserting the device into the pericardial space.

The entering step may be performed with a needle; and the translating step may be performed with a catheter. The puncturing may be performed with a wire, such as a J-tip guide wire. Desirably the puncturing further includes dilating the hole, for example with a dilator advanced over the guide wire, and preferably, the dilating is performed with a strippable sheath catheter over the dilator.

Alternatively, the puncturing may be performed with a needle inserted in the catheter and the exiting may be performed by passing a guide wire through the needle. In the method, the inserting may be performed by advancing the device along the guide wire and may further include retracting the guide wire after advancing the device to a desired location within the pericardial space.

The method may comprise the addition step of sealing the hole formed in the atrial lateral wall, such as by abutting first atrial seal means in the atrium against the atrial wall over the hole formed therein. The first atrial seal means may desirably be a cardiac lead having a skirt radially projecting therefrom.

The sealing step may be further performed by advancing second atrial seal means through the hole formed in the atrium and abutting the second seal means against the atrial wall exterior the atrium over the hole formed therein, thereby sealing the hole between the first and second atrial seal means; wherein the first atrial seal means is an outer member atrial seal attached to a cardiac lead outer member and the second atrial seal means is attached to a cardiac lead middle member.

The method may further comprise positioning the device in the pericardial space after the inserting step whether or not the sealing step is performed. The positioning may be performed by advancing a J-tip guide wire into the pericardial space and moving the device along the guide wire.

The method may further comprise injecting fluid into the pericardial space after the positioning step so as to expand the pericardial space.

The present invention method for the transvenous implantation of a cardiac defibrillator lead through a vein having a lumen into a pericardial space surrounding a cardium having an atrium with an atrial lateral wall may comprise entering the vein; translating a catheter through the vein lumen to the atrium; abutting the catheter against the atrial lateral wall and passing a needle through the catheter, puncturing the atrial lateral wall with the needle and forming a hole in the wall; routing a J-tip guide wire through the needle and exiting the atrium through the hole into the pericardial space positioning the guide wire into the pericardial space; and withdrawing the catheter and needle from the patient. After the withdrawing, the method further includes dilating the hole in the wall with a dilator and exiting the atrium space through the hole into the pericardial space with a sheath catheter; and withdrawing the dilator from the patient. The method further includes advancing along the guide wire through the sheath a cardiac defibrillator lead having an elongated hollow first member having a tip on one end thereof, the first member being coupled to an expandable conductive electrode sheet and a middle member nested over the first member proximal the tip; advancing along the guide wire an outer member nestable over the first member, having an outer member atrial seal, the seal having a skirt radially projecting therefrom; removing the sheath catheter from the patient; and abutting the seal against the inner atrial wall over the hole formed therein. The next step involves retracting the guide wire from the patient; retracting the middle member while advancing the outer member and abutting the middle member against the outer atrial wall over the hole formed therein, thereby sealing the hole between the middle member and the outer member atrial seal; injecting fluid in the pericardial space after positioning, so as to expand the pericardial space; and expanding the defibrillator electrode sheet into the pericardial space.

The present invention method for the transvenous implantation of a device through a vein having a lumen into a pericardial space surrounding a cardium having an atrium and an atrial lateral wall may comprise entering the vein; translating through the vein lumen to the atrium; anchoring onto the atrial lateral wall; and puncturing the atrial lateral wall and forming a hole therein. After the puncturing, the method further comprises exiting the atrium through the hole to the pericardial space; and inserting the device into the pericardial space.

The anchoring may be performed with a fixation catheter having an anchoring screw on the catheter, with a suction catheter, or with a bioptome catheter.

The puncturing may be performed with a wire, such as a J-tip guide wire. The puncturing may include advancing the guide wire while simultaneously retracting the catheter. Also, the puncturing may further include dilating the hole, such as with a dilator advanced over a guide wire or with a strippable sheath catheter over the dilator.

The inserting may be performed by advancing the device along a guide wire and may further include retracting the guide wire after advancing the device to a desired location within the pericardial space. The method may further comprise injecting fluid into the pericardial space after the inserting so as to expand the pericardial space.

The invention also includes a method for the transvenous repair of a wound in the atrial lateral wall of a patient through a vein having a lumen comprising entering the vein; translating through the vein lumen to an atrium of the patient's cardium with a catheter; anchoring the catheter onto the atrial lateral wall over the wound; translating a blood clot through the catheter to the wound; compressing the blood clot into the wound; and removing the catheter.

The following examples are illustrative of the cardiac leads and method for transvenous implantation of cardiac leads of the present invention but they are in no way are intended to restrict the scope of the claims hereto.

Referring generally to FIGS. 1–13, and 20–23, the defibrillator system of the present invention has means for transferring electrical energy (not shown) to at least one defibrillator cardiac lead, which is electrically coupled to a lead electrode. The means for transferring electrical energy has any construction known to those skilled in the art and is desirably implantable within a patient. The means for transferring electrical energy may have a rechargeable battery power source for storing electrical energy and it may be a cardiac pacer coupled thereto. The defibrillator system may desirably have means for sensing the onset of a cardiac arrythmia known to those skilled in the art. Should the system detect the onset of an arrythmia, it can commence defibrillation by transferring electrical energy to the cardiac lead electrodes. The patient can then recharge the defibrillator system batteries by any means known to those skilled in the art.

FIGS. 1-3 show a cardiac lead 1 of the present invention, implantable in a patient's pericardial space having an elongated first member 3 having a tip 4, an axial bore 5 therethrough, and implantable objects or devices, which as shown are conductive defibrillator system electrode sheets 7, that are coupled to the first member. The term electrode sheets can also mean a conductive mesh screen or other conductive coated surface. As can be appreciated by those skilled in the art, other implantable objects, such as sensing instruments or surgical tools, can be substituted for the electrode sheets 7. As shown by comparing FIGS. 1 and 3, the electrodes 7 are expandable from a collapsed position generally in contact with the lead 1, (FIG. 1), to an extended position generally away from the lead (FIG. 3). As shown in FIG. 2, the electrode sheets 7 are rolled in the collapsed position and unroll to the extended position shown in FIG. 3. The electrode sheets 7 may also be folded into the collapsed position. Any means of gathering the electrode sheets 7 is contemplated in the invention.

The lead 1 also has means for expanding the electrode sheets 7 from the collapsed to the extended position that is coupled to the electrodes and as shown in FIGS. 1 and 3, the means for expanding is closed ducts 9 connected to hydraulic tubes 11. Ducts 9 and tubes 11 receive pressurized fluid, such as saline solution, and forcing pressurized fluid through the ducts extends the electrode sheets 7.

The lead 1 also has conductive wires 13 connected to the electrodes 7 and coupled to the defibrillator system means for transferring electrical energy. The wires 13 are preferably attached to the first member 3. In the preferred embodiment, lead 1 has a middle member 15 nested over the first member 3 proximal tip 4 and as shown in FIGS. 1-3, the middle member is reciprocable from a first position proximal the tip (FIG. 1), to a second position distal the tip (FIG. 3). The middle member 15 also has cavities 17 adapted for receipt of the electrode sheets 7 therein. When the middle member 15 is in the first position proximal the tip 4, the electrode sheets 7 are sheltered within the cavities 17, which prevents inadvertent electrode expansion of possible snagging contact with tissue during transvenous implantation, and when the middle member is in the second, distal position, the electrodes are exposed and may be expanded generally outside the lead 1.

The middle member 15 preferably has a middle member atrial seal means 19 such as a middle member atrial seal face 21, which preferably has a fabric surface 23 thereon for sclerosis of cardiac tissue therein. The preferred fabric is DACRON (R) polyester.

In the preferred embodiment, the lead 1 also has an outer member 25 nested over the first member 3 proximal the middle member 15 and also as shown, the outer member is nested over a portion of the middle member and is reciprocable with respect to the middle member atrial seal means 19. The outer member 25 has an outer member atrial seal means 27 and as shown the seal has a skirt 29 radially projecting from the outer member having a face 31 with a fabric surface 33, which fabric is preferably DACRON (R) polyester.

FIGS. 4-7 show another embodiment of a cardiac lead 35, implantable in a patient's pericardial space, wherein the implantable object is an electrode sheet 37 that is generally a sector or fan-shaped arc of a circle coupled to hollow first member 39. Conductive wires for coupling the electrode sheet 37 to the defibrillator system are not shown. The means for expanding the electrode sheet 37 are ribs 41 pivotally coupled to the first member 39 and rib extension means, which as shown in FIGS. 4 and 5 is a pair of wires 43 coupled to the ribs and the middle member 45. The ribs 41 may have sclerosis points 47 thereon to stimulate fixation to tissue.

The middle member 45 has a cavity 49 that shelters the electrode sheet 37 when the middle member is reciprocated proximal the tip 51. After reciprocating middle member 45 distal the tip 51, thereby exposing the electrode sheet 37, a biasing action on the wires 43 pivots the ribs 41 and extends the electrode sheet to its extended position. The electrode 37 extension sequence is shown in FIGS. 4-7. The rib biasing means can also be leaf springs attached to the ribs 41 and the first member 39 (not shown). The fan-shaped electrode sheet of this embodiment can also be expanded by closed ducts, hydraulic tubes and pressurized fluid, such as shown in FIGS. 1-3.

The middle member 45 shown in FIGS. 4 and 5 also has a middle member atrial seal 53 which has a radially projecting skirt with a seal face having a fabric surface thereon, similar in construction to the outer member atrial seal 27 in FIG. 1. Also shown are outer member 54 with an atrial seal 54A, similar to seal 27 in FIG. 1.

FIGS. 8-10 show another embodiment of the cardiac lead 55 of the present invention, for implantation into a patient's atrium rather than in the pericardial space. The implantable object is a circular umbrella-like electrode sheet 57 having extension means including a reciprocable collar 59 nested on the first member 61, ribs 63 and stays 65, coupling the ribs and the collar so that reciprocation of the collar reciprocates the stays and in turn pivots the ribs in umbrella-like fashion. The collar reciprocating means is a threaded member 67 that threads into the collar 59 and is rotated by a hollow cable 69 that is nested within the first member axial bore 71. Rotating cable 69 translates collar 59 along the cable threaded member 67. Alternatively, the collar reciprocating means can be one or more wires running through the first member axial bore. In lieu of collars, ribs and stays, the electrode sheet 57, can be expanded by pressurized fluid, ducts, and tubes, such as shown in FIGS. 1-3.

FIGS. 11 and 12 show a cardiac lead embodiment 72 similar to that shown in FIGS. 8-10, wherein the electrode sheet 72A is extended by ribs 72B and a reciprocable sleeve 72C. When the electrode sheet 72A is in the collapsed position, it is captured within middle member 72C. To extend the electrode sheet 72A, the middle member 72C is first retracted relative to the first member 72D to expose the sheet and ribs 72B. Next, the middle member 72C is advanced relative to the first member 72D inside the umbrella-like sheet 72A so that the middle member pivots the ribs in umbrella-like fashion. Conductive wires for coupling the electrode 72A to the defibrillator system are not shown. The lead 72 also has a helical screw tip 72E attached to the end of the first member 72D that is useful for screwing into the intra-atrial septum, so that the lead can function as an atrial electrode.

FIG. 13 shows a cardiac lead 73 embodiment similar to that shown in FIGS. 8-10, with the addition of a helical screw tip 75 on the tip of the collar reciprocating threaded member, that is useful for screwing into the intra-atrial septum. Upon expanding the electrode sheet in the right atrium, the lead can function as an atrial electrode. The electrode is implanted transvenously by entering the subclavian vein and translating the lead 73 through the subclavian vein through the superior vena cava 77 and into the right atrium 79, shown schematically in the partial cut-away view. The lead 73 is then screwed into the atrial septum at any desired location and the electrode sheet is expanded. The lead 72, shown in FIGS. 11 and 12, may be similarly implanted.

The umbrella-like electrode embodiments shown in FIGS. 8-10 and 13 do not have a middle member or outer member, though if desired such members may be nested over the first member. Conductive wires for coupling the electrode to the defibrillator system are not shown.

The cardiac leads of the present invention can be used with any combination of electrode sheet, or other implantable objects such as sensing instruments, or surgical tools, and any combination of middle or outer member embodiments or atrial seal embodiments described herein. It is also desirable to construct the atrial seals with radio-opaque markers therein so that their position can be monitored under fluroscopy during implantation.

It is contemplated that the defibrillator system of the present invention would utilize certain combinations of cardiac lead embodiments described herein, so long as there are at least two electrodes implanted in the patient's cardiovascular system. By way of example, the intra-atrial leads 55, 72 or 73, shown in FIGS. 8-13, may be paired with the fan-shaped pericardial electrode 35, shown in FIGS. 4-7 and 20, or a single electrode version of the lead 1 shown in FIGS. 1-3. As another alternative, the double electrode pericardial lead 1, shown in FIGS. 1-3 and 21, may be utilized without an intra-atrial electrode.

The present invention also features methods for the transvenous insertion of devices into the pericardial space of a cardium, such as cardiac leads of the present invention, having defibrillator electrodes, which methods are shown schematically in FIGS. 14-23. In these figures, the superior vena cava 77, cut-away view of the right atrium 79, the atrial lateral wall 81, the pericardial space 83, and the pericardium 85 are shown in simple schematic form, understandable to those skilled in the art.

Using sterile surgical techniques, a subcutaneous pocket is formed in the right subclavian area under local anesthesia and a catheter is translated through the lumen of the subclavian vein and in turn through the superior vena cava 77 to the right atrium 79. While the subclavian vein is the preferred entry vein into the cardiovascular system, because it is an entry technique well known to surgeons, any other convenient vein that connects to the right atrium, such as the femoral vein, the internal jugular vein or the external jugular vein may be used.

Figures 15, 16:
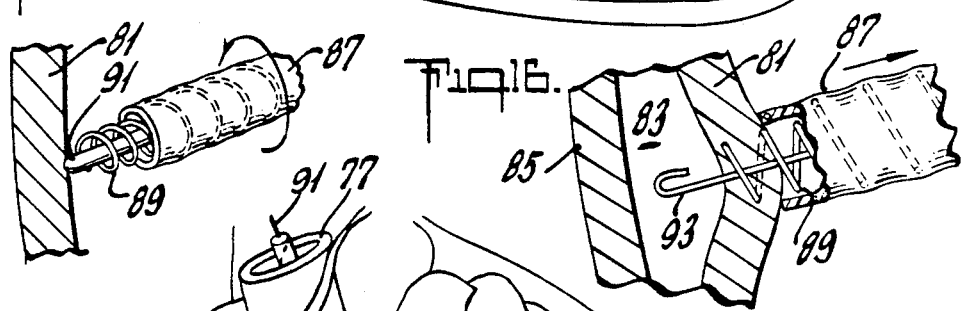
FIG. 15 is a detailed elevational view of the fixation catheter and stylus, shown in FIG. 14.
FIG. 16 is a detailed elevational view of the fixation catheter and a J-tip guide wire puncturing the atrial lateral wall to form a hole therein.
Figure 14:
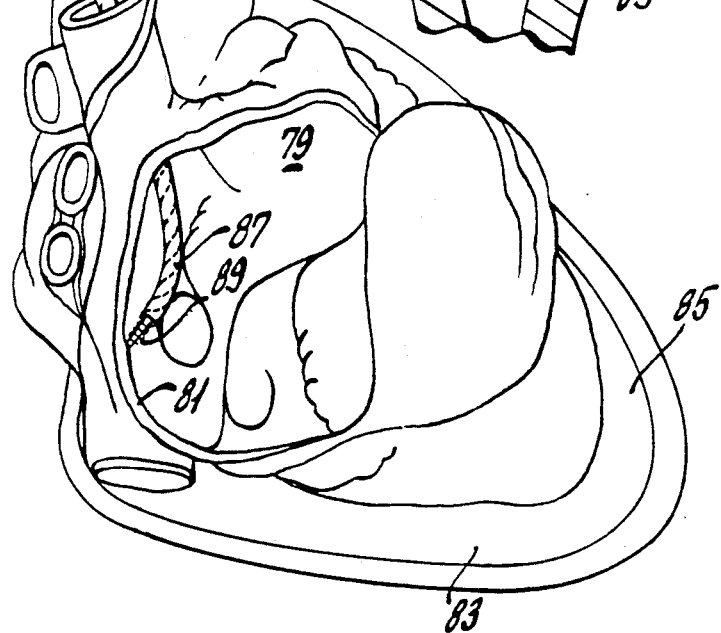
FIG. 14 is a schematic, elevational cut-away view of a right atrium, showing a fixation catheter and stylus abutting the atrial lateral wall.
Figure 24:
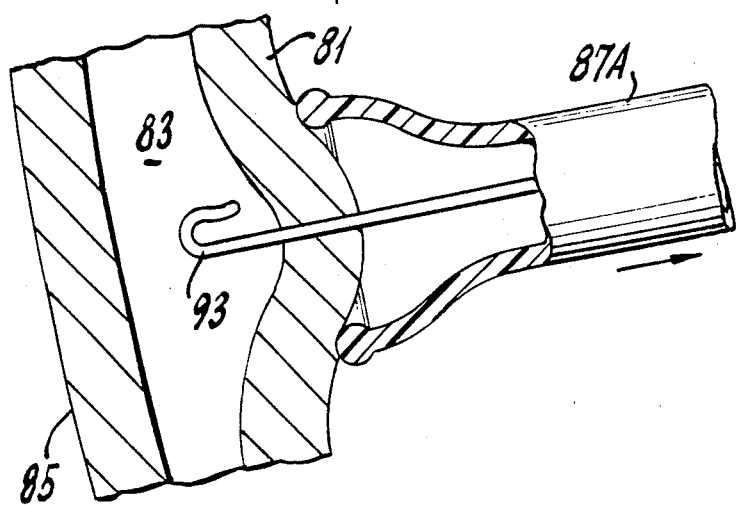
FIG. 24 is a detailed elevational view of a suction catheter and a J-tip guide wire puncturing the atrial lateral wall to form a hole therein.
Figure 25:
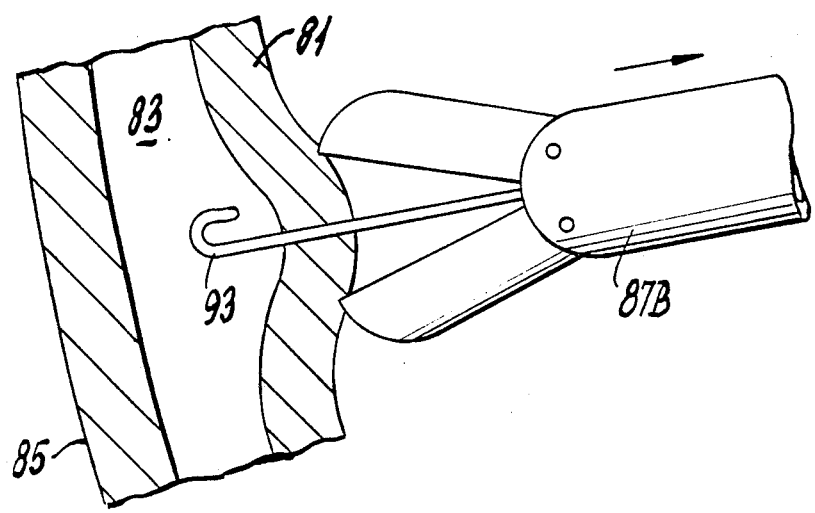
FIG. 25 is a detailed elevational view of a bioptome catheter and a J-tip guide wire puncturing the atrial lateral wall to form a hole therein.

As shown in FIGS. 14 and 15, the preferred catheter is a fixation catheter 87 having a helical anchoring screw 89 projecting from the tip thereof, for anchoring into the atrial lateral wall 81. A preferred construction of the fixation catheter is a plastic coated helical spring with a few turns of the spring left exposed to form the anchoring screw. Alternatively, any other catheter that can be anchored to the atrial lateral wall, such as a suction catheter 87A or a bioptome catheter 87B may be used to perform the procedure as shown in FIGS. 24 and 25, respectively.

As shown in FIGS. 14 and 15, a stylus 91 is inserted into the fixation catheter 87, to aid in abutting the catheter against the atrial lateral wall. Next, the screw 89 is anchored into the patient's atrial lateral wall 81, by rotating the catheter 87. Once the catheter 87 is anchored into the atrial lateral wall 81, the stylus 91 is removed, and a wire, such as a J-tip guide wire is inserted into the catheter.

Figure 17:
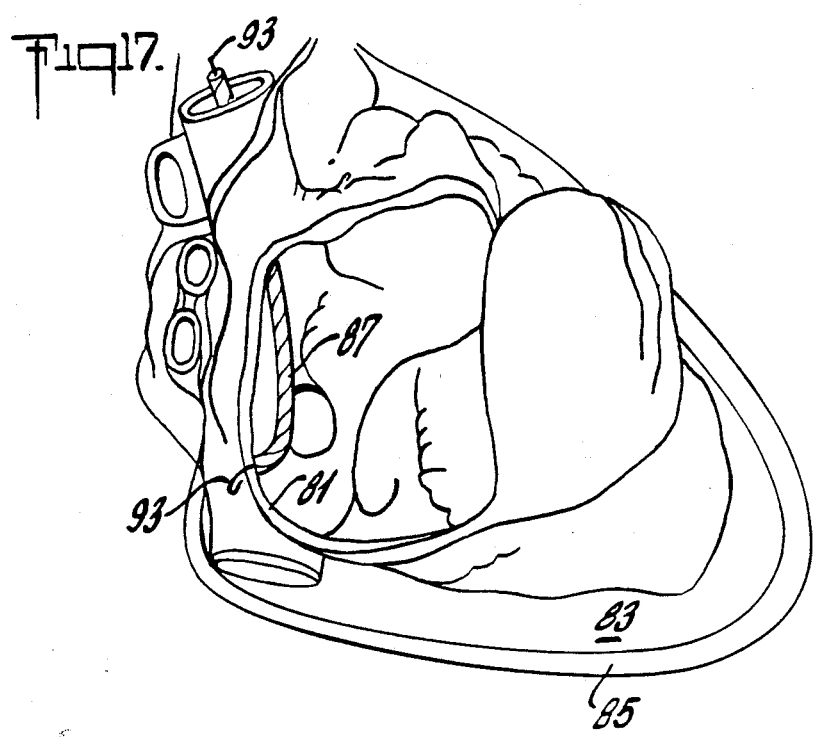
FIG. 17 is a schematic view of similar to FIG. 14, showing the J-tip guide wire entering the pericardial space.

The next step in the procedure is puncturing the atrial lateral wall 81 with the J-tip guide wire 93, as shown in FIGS. 16 and 17. The preferred puncturing technique is to retract the fixation catheter 87 while simultaneously advancing the guide wire 93, so that the atrial lateral wall 81 is separated from the pericardial sac 85, thereby minimizing the likelihood of guide wire over-penetration through the pericardium. If desired, the guide wire 93 may be removed and one or more large diameter guide wires may be in turn advanced through the atrial lateral wall to dilate the hole formed therein.

The guide wire 93 is then positioned at any desired location in the patient's pericardial space 83, though the physician performing the procedure may elect to delay guide wire positioning until later in the procedure.

As an alternative atrial lateral wall puncturing method, a needle may be used to form a hole in the lateral wall by inserting the needle into the fixation catheter. The needle preferably has a blunt, square end that can cut through atrial muscle but not the fibrous pericardium. A suitable needle is a section of 18 gauge needle having a length of approximately 0.25 inch mounted on the tip of a hollow atriotomy tool, so that objects, such as guide wires may be passed through the atriotomy tool and the needle mounted thereon. A guide wire, such as a J-tip guide wire, is passed though the needle and the hole in the atrial lateral wall and the wire thereby exists the atrium into the pericardial space 83 for positioning therein, after which time the needle is removed.

If for any reason after puncturing the atrial lateral wall, the physician decides to terminate the implantation procedure, the puncture site can be easily repaired by preparing a small autologous blood clot (i.e., with the patient's own blood) and forcing the clot into the atrial perforation. A ramrod-like catheter can be used to force the clot through the active fixation catheter into the puncture site. Then the ramrod is retracted from the fixation catheter and the catheter is in turn withdrawn from the patient by unscrewing same.

As a next preferred step in the procedure, the fixation catheter 87 is withdrawn and the hole formed in the atrial lateral wall 81 is then dilated to a larger diameter, to facilitate placement of implantable objects into the patient's pericardial space 83. However, the physician performing the procedure may elect to remove the catheter 87 after dilation.

Figure 18:
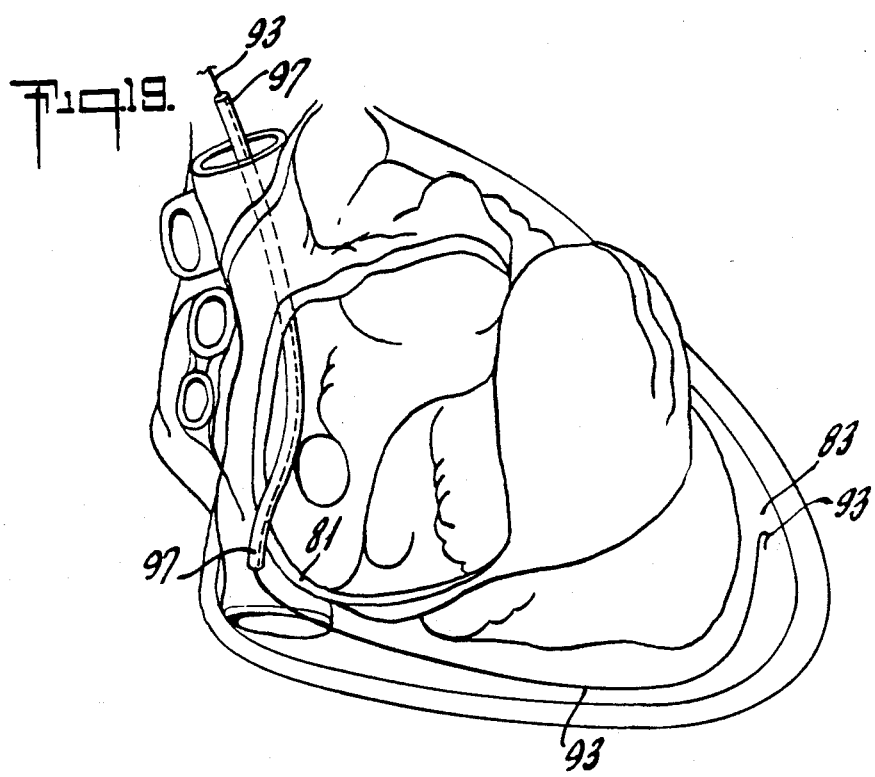
FIG. 18 is a detailed elevational schematic view showing dilating the puncture hole in the atrial lateral wall with a dilator and sheath catheter.
Figure 18:
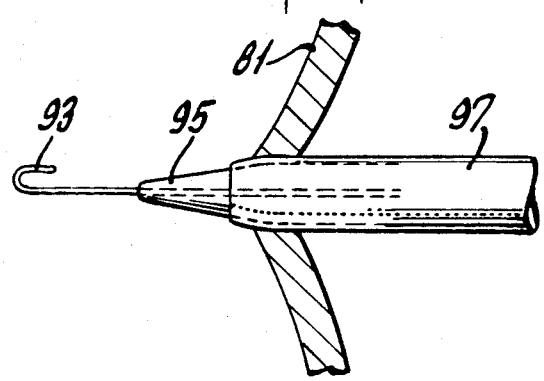

The preferred dilating device is shown in FIG. 18, and is a generally conically-shaped, blunt tipped dilator 95 that has a hollow bore for passage over the J-tip guide wire 93. A strippable sheath catheter 97 of a type known to physicians is fitted over the dilator 95 prior to insertion into the patient. After dilation is completed, the dilator 95 is withdrawn from the patient, but the sheath catheter 97 is left in place, partially in the pericardial space 83, as shown in FIG. 19. The sheath catheter 97 facilities passage of implantable objects over the guide wire 93 from outside the patient into the pericardial space. Any implantable device may now be positioned into the pericardial space 83.

Figure 20:
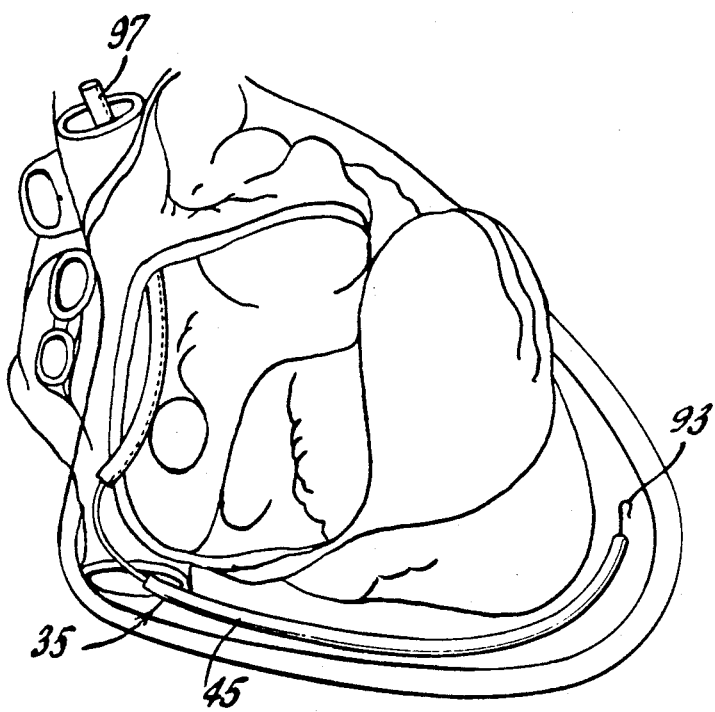
FIG. 20 is a schematic view similar to FIG. 19, showing the insertion of a portion of a cardiac lead of the present invention through the sheath and into the pericardial space.

In FIGS. 20-23, the device positioned in the pericardial space is a cardiac lead of the present invention 5 having retractable defibrillator electrodes and atrial seals. FIGS. 20-22 show the cardiac lead 35 of FIGS. 4-7 advanced along guide wire 93 with the middle member 45 reciprocated in the position proximal the first member tip 51, before removal of the guide wire. In FIG. 20, the sheath catheter 97 remains in place during implantation of the first member 39, middle member 45 and outer member 54; then the catheter is withdrawn. The outer member 54 is positioned in the right atrium with the outer member atrial seal abutting the hole formed in the atrial lateral wall 81 as shown in FIG. 21.

Upon removal of the guide wire 93 from the axial bore of the first member 39, devices (such as medical instruments, including fiber optic scopes and catheters) or implantable objects may be transvenously passed through the lead into the pericardial space 83. As a next step in the procedure, the middle member 45 is reciprocated to its rearmost position distal the first member tip 51, thereby slidably capturing the hole formed in the atrial lateral wall between the middle member atrial seal 53 and the outer member atrial seal 54A; see FIG. 22. Using atrial seals constructed with radio-opaque markers allows fluoroscopic verification that the seals are properly aligned during the sealing step.

The next step in the procedure is optional and involves injecting fluid, such as saline solution, into the lead axial bore to expand the pericardial space 83 and allow more positioning room for devices, such as expandable defibrillator electrodes. The fluid injection is a purely temporary measure and the excess fluid is removed once the electrodes or other devices are properly positioned. The excess fluid can be removed through the lead axial bore or by other percutaneous techniques, such as for example, a needle inserted under the sternum through the pericardium.

Next, the implanted objects are positioned, such as the extended electrodes in FIGS. 22 and 23. In FIG. 22 there is shown a cardiac lead 35 with a single fan-shaped defibrillator electrode 37 that would be paired with an intra-atrial defibrillator cardiac lead 55, 72 or 73, as shown in FIGS. 8-13. FIG. 23 shows a pair of right and left ventricular defibrillator electrodes 7, constructed as shown in FIGS. 1-3. The electrodes 37 and 7, respectively shown in FIGS. 22 and 23 are extended as described with regard to apparatus FIGS. 1-12.

What is claimed is:

1. In a patient, a method for the transvenous implantation of a device through a vein having a lumen into a pericardial space surrounding a cardium having an atrium and an atrial lateral wall comprising:
   entering the vein;
   translating through the vein lumen to the atrium;
   anchoring onto the atrial lateral wall;
   puncturing the atrial lateral wall and forming a hole therein;
   exiting the atrium through the hole to the pericardial space; and
   inserting the device into the pericardial space.

2. The method of claim 1, wherein the anchoring is performed with a fixation catheter having an anchoring screw on the catheter.

3. The method of claim 1, wherein the anchoring is performed with a suction catheter.

4. The method of claim 1, wherein the anchoring is performed with a bioptome catheter.

5. The method of claim 1, wherein the puncturing is performed with a wire.

6. The method of claim 5, wherein the wire is a J-tip guide wire.

7. The method of claim 6, wherein the puncturing includes advancing the guide wire while simultaneously withdrawing the catheter.

8. The method of claim 1, wherein the puncturing further includes dilating the hole.

9. The method of claim 8, wherein the dilating is performed with a dilator advanced over a guide wire.

10. The method of claim 9, wherein the dilating is performed with a strippable sheath catheter over the dilator.

11. The method of claim 1, wherein the inserting is performed by advancing the device along a guide wire.

12. The method of claim 11, wherein the inserting further includes retracting the guide wire after advancing the device to a desired location within the pericardial space.

13. The method recited in claim 1 further comprising injecting fluid into the pericardial space after the inserting so as to expand the pericardial space.

14. In a patient, a method for the transvenous repair of a wound in the atrial lateral wall of a patient, through a vein having a lumen comprising:
   entering the vein;
   translating through the vein lumen to an atrium of the patient's cardium with a catheter;
   anchoring the catheter onto the atrial lateral wall over the wound;
   translating a blood clot through the catheter to the wound;
   compressing the blood clot into the wound; and
   removing the catheter.

* * * * *